United States Patent [19]

North, Jr.

[11] Patent Number: 4,844,610
[45] Date of Patent: Jul. 4, 1989

[54] BACKFLOW ISOLATOR AND CAPTURE SYSTEM

[75] Inventor: Howard North, Jr., Los Gatos, Calif.
[73] Assignee: Becton, Dickinson and Company, Franklin Lakes, N.J.
[21] Appl. No.: 188,582
[22] Filed: Apr. 29, 1988
[51] Int. Cl.⁴ .......................................... G01N 33/48
[52] U.S. Cl. ...................................................... 356/73
[58] Field of Search ................... 356/39, 72, 73, 246, 356/338; 73/865.5, 864.81

[56] References Cited

U.S. PATENT DOCUMENTS 3,710,933  1/1973  Fulwyler et al. .................. 356/73
4,071,298  1/1978  Falconer .......................... 356/73
4,352,558  10/1982  Eisert ............................. 356/73

Primary Examiner—Richard A. Rosenberger
Attorney, Agent, or Firm—Aaron Passman

[57] ABSTRACT

A flow apparatus for the analysis of particles passing with a liquid substantially one at a time through an analysis region includes a backflow isolator and capture system to catch any liquid and particles dripping from the analysis region. The backflow isolator and capture system is activated by an unlocking support for the sample test tube carrying the supply of liquid and particles. The support is also an operator for a pump and a pressure vent valve whereby liquid, particles and aerosols cannot escape. A method for isolating and capturing backflow of a supply of particles to be analyzed includes steps of venting the air supply, moving a test tube support and activating a pump.

18 Claims, 4 Drawing Sheets

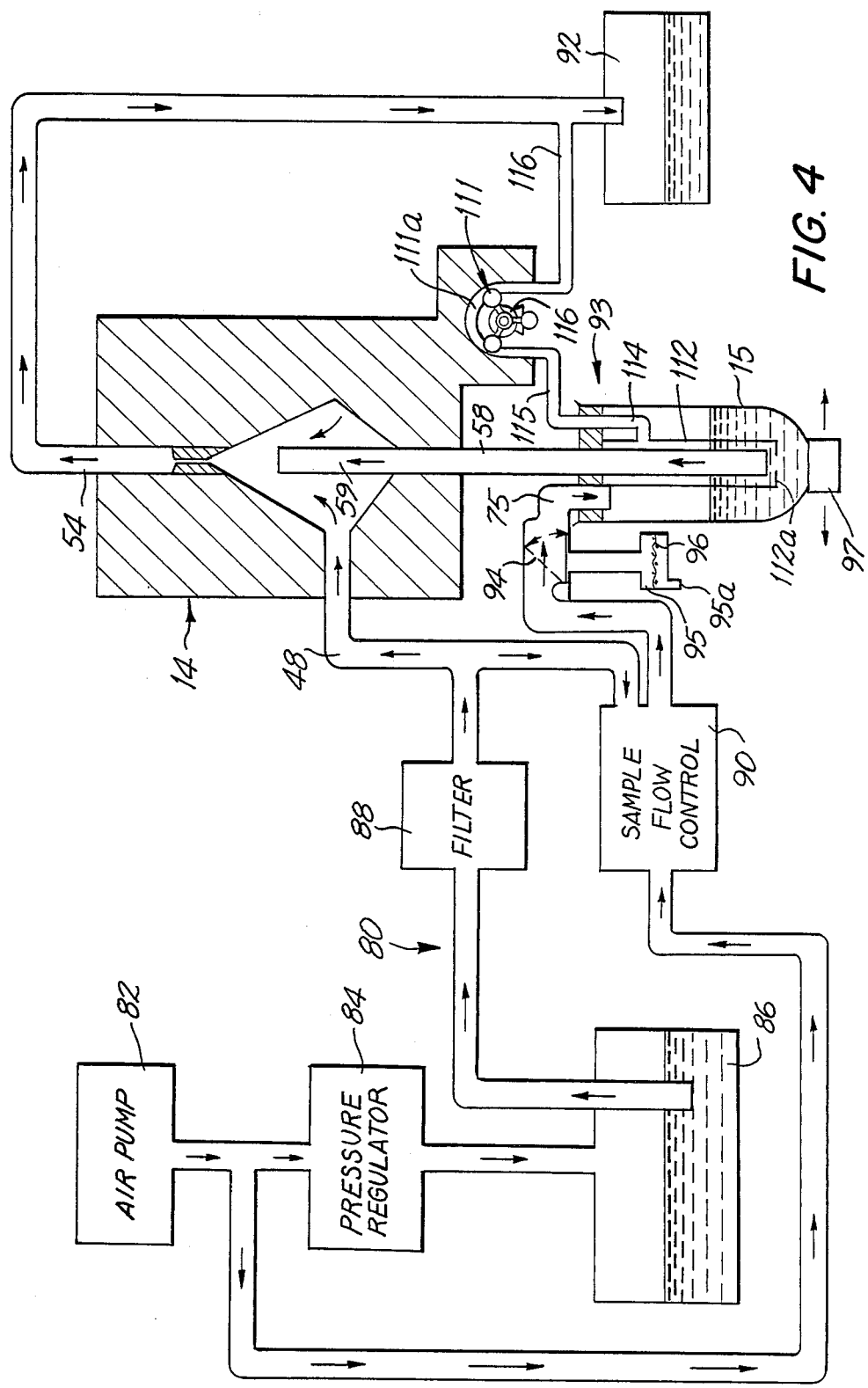

BACKFLOW ISOLATOR AND CAPTURE SYSTEM

BACKGROUND OF THE INVENTION

1. Field of the Invention

The present invention relates to a backflow isolator and capture system for a particle flow through apparatus which includes a unique valve operator and pump control, and more particularly, concerns a flow cytometer for determining one or more characteristics of particles flowing through the cytometer with such a backflow isolator to provide safety in connection with changing sample test tubes and cleaning the flow path. The method of isolating and capturing backflow is also a part of the present invention.

2. Background Description

There are a number of cell or particle analyzing devices using flow cytometer equipment and techniques which rely on hydrodynamically focused fluid flow through an analysis orifice where the specific characteristics of the flowing cells or particles can be determined. Flow analysis of particles has been used in the determination of the variety of characteristics of individual particles. This analysis is most useful in determining characteristics of cells for the collection of information which would aid in areas of research, hematology, immunology and the like. The researcher, for example, could be interested in determining specific characteristics of the individual cells where those cells need to be classified, identified, quantified and perhaps sorted for further investigations or analysis.

One commercially available flow cytometer which relies on a hydrodynamically focused fluid system is known as the FACScan ™ instrument sold by Becton Dickinson Immunocytometry Systems, Mountain View, Calif. The FACScan ™ instrument rapidly analyzes cells on the basis of fluorescence and light scatter properties. Analysis is accomplished by introducing cells in suspension to the center of a focused liquid stream and causing them to pass, one at a time, through a focused light from a high power lamp or laser. Each cell is individually characterized by its light scatter signals and by the intensity and color of fluorescence emitted while it is illuminated.

In the aforementioned flow cytometer, a sheath liquid focuses the particles or cells as they pass through the orifice associated with the analyzing or counting capabilities. U.S. Pat. Nos. 4,503,385 and 4,526,276 describe particle analysis systems in which particles flowing in a stream are enveloped in a sheath liquid which focuses and confines the sample liquid (with the particles or cells) to the center of the flowing stream. U.S. Pat. No. 4,110,604 describes a particle density measuring system in which particles flowing in a stream are enveloped in a sheath liquid which focuses and confines the sample fluid (with the particles) to the center of the flowing stream.

In the presently known and available flow through equipment, electrically operated pumps, syringe pumps or the like are used in the fluidics of the system to move the liquid and particle flow through the flowcell analysis orifice and passageways. The usual operation for these pumps is to force or draw liquid with particles from a sample test tube through a sample capillary uptake tube centered in the sheathing liquid flowing in the direction of the particle analysis orifice. The Assignee of the present application has co-pending applications, U.S. Ser. No. 866,003 filed May 22, 1986, disclosing a housing for a flow cytometer with a particle unclogging feature and U.S. Ser. No. 125,095 filed Nov. 25, 1987 disclosing a sheathed particle flow controlled by differential pressure.

Particle analysis instruments often use air pressure to cause particle flow from a sample containing test tube into an analysis region of the instrument where a pressurized ensheathing liquid hydrodynamically focuses the particle stream for passage through the analysis region. Upon removal of the sample containing test tube the ensheathing liquid and particles can backflow through the sample uptake tube and drip off the end thereof. With certain samples dripping liquid and particles present a possible biohazard. In particular, the sample can include potentially biohazardous cells which could drop, splatter and contact the operator or the work area. The air pressure used to drive the particles up the uptake tube has to be safely vented to avoid release of aerosols containing potentially biohazardous cells. This is a particularly great problem when removing the sample containing test tube which often contains residual air pressure in addition to the sample. Another concern is the possibility of the air pressure supply for the sample containing test tube causing the test tube to be unexpectedly blown off the flow cytometer housing.

With the foregoing in mind, improved techniques for safely handling the changing of sample containing test tubes in particle flow through equipment are still being sought. Such improvements in test tube handling should preferably be included in the particle flow through apparatus so that there are no biohazardous particles, vapors or liquids released. It is toward such an improvement that the present invention is directed.

SUMMARY OF THE INVENTION

A preferred form of the present invention includes a sample backflow isolator for a flow cytometer having a body with a passage therethrough for particles which are to be analyzed. The passage includes a pre-analysis portion and an analysis portion and a post-analysis portion. An uptake tube in the pre-analysis portion is connected in fluid communication with the passage and is adapted for providing samples of particles from a test tube to the analysis portion. A backflow capture means is associated with the uptake tube and a pump for drawing fluid from the uptake tube after the flow from the test tube to the analysis portion has been terminated.

The backflow capture means is connected to the pump to provide fluid communication between the backflow capture means, the pump and the post-analysis portion. Air is used to drive samples of particles through the analysis portion. A filtered vent is connected to the test tube by a valve means for relieving any air pressure remaining in the test tube for the sample. There is an operator disposed to support and lock the test tube to the body of the flow cytometer and operate a switch which changes the valve means to connect the filtered vent to the test tube. The switch also operates the pump.

Another form of the backflow isolator and capture system includes a flow cell with an orifice to permit the passage of substantially one particle at a time through the analysis portion and a concentrically disposed outer tube arranged to encircle the uptake tube and operative to draw away residual samples of particles. A still further form of the backflow isolator includes means for permitting light to be directed at the orifice at an angle orthogonal to the direction of particle flow through the flow cell. A further refinement of the backflow isolator has, in the means for permitting light, a recess for positioning a lens adjacent the flow cell.

The backflow isolator filtered vent preferably includes a filter capable of capturing aerosols released from the test tube when the valve connects the test tube to the filtered vent. The valve of the backflow isolator can have an operator activated solenoid for closing the air supply which pressurizes the test tube containing particles. The vent is then connected to the test tube. The valve and pump are simultaneously activated. A still further aspect of the system includes a device where the inner end of the uptake tube is located within a tapered entrance to the analysis portion near the pre-analysis portion. The backflow isolator and capture system may be used wherein a sheathing liquid is introduced into the pre-analysis portion about the uptake tube inner end to provide a sheathed flow of particles hydrodynamically focused along an axis of the passageway towards the analysis portion away from the backflow capture means.

The backflow isolator and capture system might be included in a particle flow through apparatus with a body member having a passageway therethrough including an analysis region through which substantially one particle at a time may pass in the direction of flow when the apparatus is operating. A supply of particles connected in fluid communication with the passageway and a sheathing liquid applied to the supply of particles in the passageway cooperate to provide substantially one particle at a time to the analysis region. A backflow capture means associated with the passageway draws fluid from the passageway in the direction opposite the flow during analysis. The backflow capture means operates when the particle flow through the analysis portion has been shut off. The system may include control means connected to the backflow capture means for supporting the supply of particles. The control means selectively operates the backflow capture means for removing particles from the passageway. The backflow capture means includes a pump to draw fluid from the passageway. The control means has an operator to activate the pump. The operator switches electric power to the pump and opens a solenoid valve which vents air pressure in the supply of particles through a filter.

Another more specific form of the backflow isolator is used on a flow cytometer wherein a body with a passage therethrough permits particles to flow from a pre-analysis portion to an analysis portion and a post-analysis portion. All of which portions are along the same axis through the body member. An uptake tube, with an inner end in the pre-analysis portion and outer end extending outwardly of the body for insertion into a pressurized sample supply containing liquid and particles, has a lumen extending therethrough for passage of particles toward the analysis portion. A flow cell is included in the analysis portion with an orifice sized to permit the passage of substantially one particle at a time through the analysis portion. A backflow capture means is in fluid communication with the uptake tube and the post-analysis portion and a regulating means is operatively associated with the backflow capture means for activating, connecting and directing the backflow captured from the uptake tube to the post-analysis portion.

The flow cytometer includes means for moving particles of a liquid flow stream through a body member having a passageway therethrough including an analysis region where the particles pass substantially one at a time in the direction of the flow. A beam of light is provided to illuminate the particles passing through the analysis region and a means for detecting light with respect to each moving particle and for associating the detected light with one or more characteristics of the particle are also included in the flow cytometer. A backflow capture means is included to draw backflow from the passageway when the means for moving the particles has been shut off.

A method for isolating backflow through a particle analysis apparatus has the steps of venting the air pressure applied to the liquid through a safety filter while concurrently moving a support for a sample of particles while simultaneously activating a pump connected to transport liquid and particles remaining in the analysis region to a disposal area. The method step of moving may also include pivoting the support for the sample of particles carried in a liquid to release the sample for removal. The method of venting can include connecting the remaining applied air pressure by way of a valve to the safety filter. The connecting step can include operating an electrical solenoid valve. The step of activating the pump can include closing a switch by means of moving the support.

BRIEF DESCRIPTION OF THE DRAWINGS

FIG. 4 is a schematic illustration of the relationhip of the backflow isolator operative elements and the flow paths between the element including the connections of the control with the analyzer of FIG. 1.

DETAILED DESCRIPTION

Figure 1:
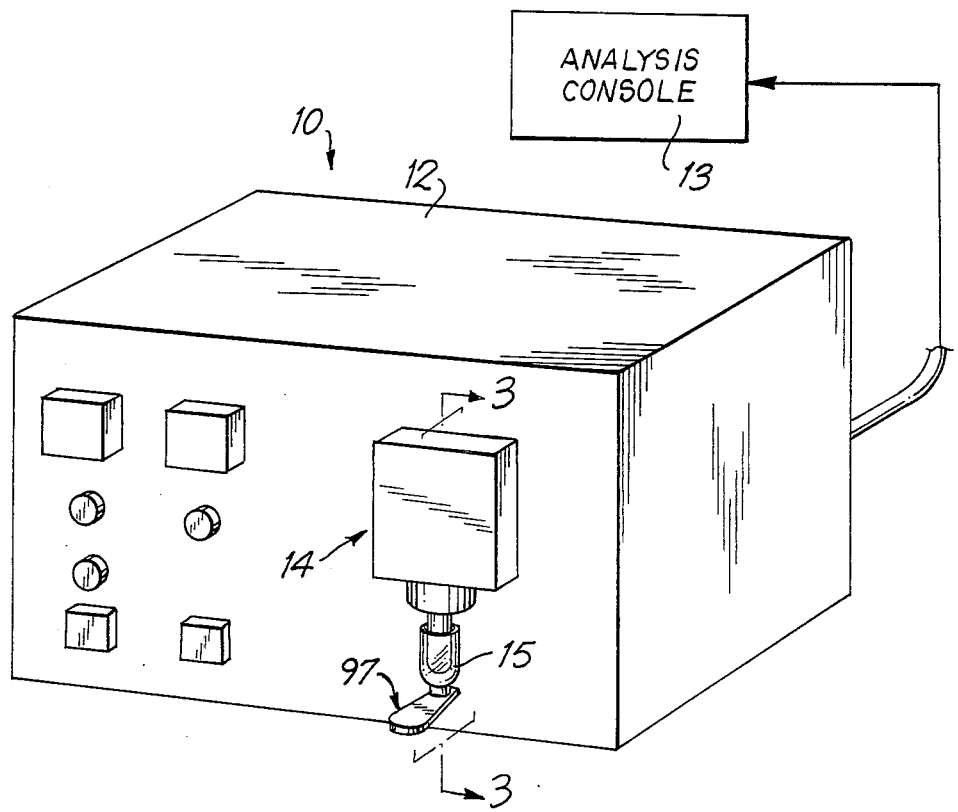
FIG. 1 is a perspective view of the preferred embodiment of a flow cytometer analyzer with a backflow isolator for use in determining one or more characteristics of particles or the like flowing in a liquid stream.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, and FIG. 1 in particular, there is illustrated a flow cytometry apparatus 10 of the present invention for determining one or more characteristics of particles or the like. Apparatus 10, for example, may be a cell analyzer which includes a liquid sampling console 12 which is constructed to contain particle or cell detection and analysis elements as hereinafter described. In particular, apparatus 10 includes a liquid sampling console 12 which is constructed to contain the particle, light scatter and fluorescence measuring components, as hereinafter described, but which is separate from the analysis console 13. It will be pointed out hereinafter that analysis console 13 includes the electrical components, display screens and other data information regarding the control and function of the apparatus 10. Liquid sampling console 12, as seen in FIG. 1, includes a flow manifold assembly in the form of a housing 14 which is designed to provide a stream of flowing liquid containing the particle to be analyzed. In the apparatus being described, the particles for analysis may be included in a test tube 15 which may be sealably engaged onto housing 14. Before describing the details of housing 14, a general description of the optical and flow elements of flow cytometry apparatus 10 will be provided.

Figure 2:
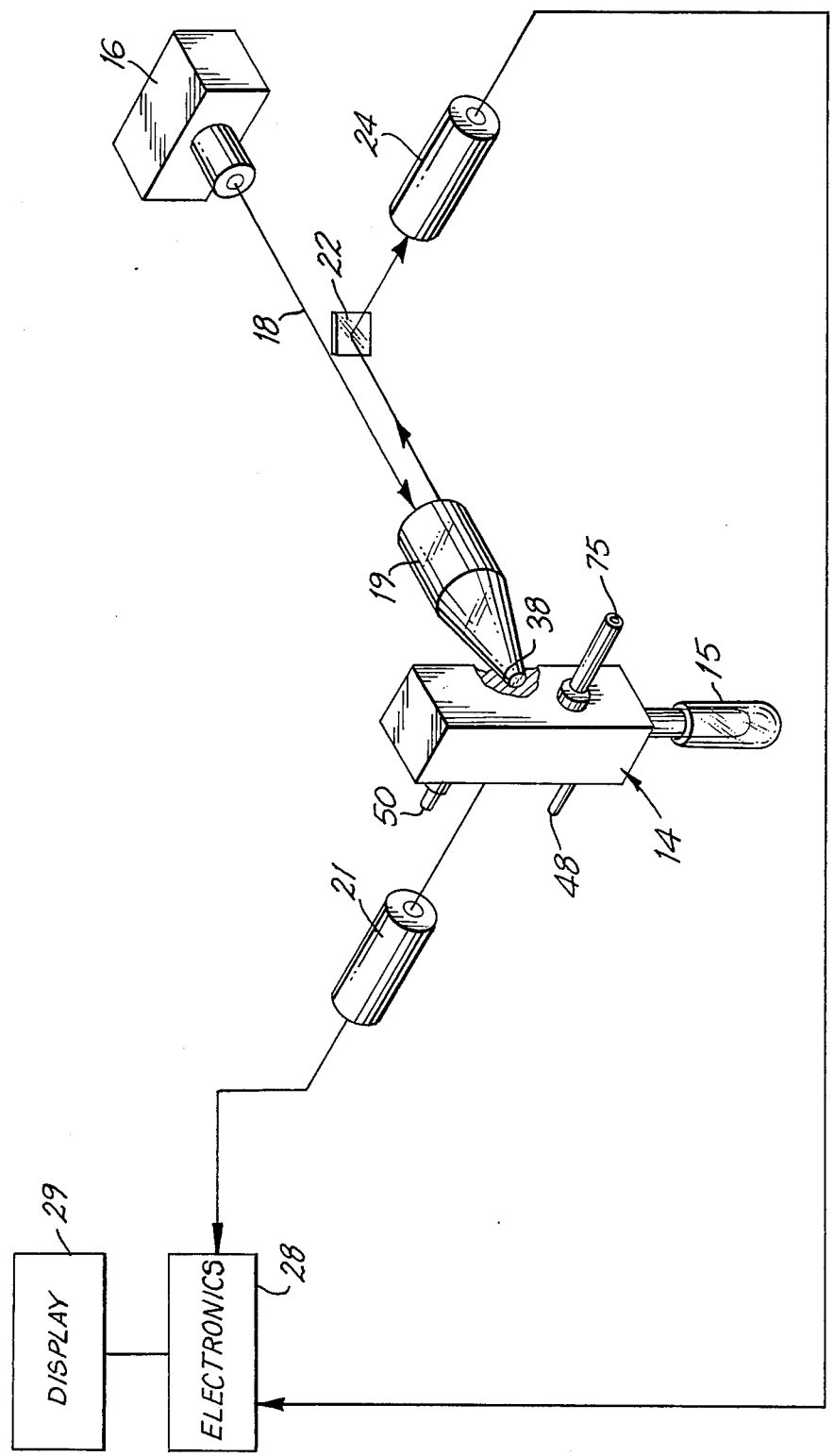
FIG. 2 is a schematic illustration of typical elements and light paths of a flow cytometer embodying the backflow isolator of the present invention.

FIG. 2 is a schematic illustration of the general optical and flow elements embodied in the preferred flow cytometer of the present invention. In addition to the general optical and flow elements of the apparatus to be described, other details of a cell analyzer apparatus useful in conjunction with the present invention are described in European Patent No. 0068404. It is understood that the housing 14 of the present invention is useful in many different types of flow cytometry or flow fluorometric equipment which measure light scatter, fluorescence, or other optical parameters for the identification, quantification or enumeration of cells, particles or the like in a sample liquid medium. As illustrated in FIG. 2, light energy is provided for the flow cytometer by a light source 16 such as a laser which provides a coherent beam of light at a singular wavelength or an arc lamp, such as a mercury or xenon arc lamp, which provides an incoherent beam of light comprising a broad spectrum of wavelengths.

Excitation energy is transmitted in the flow cytometer by a beam of light 18 produced by light source 16. Typically, the beam of light passes through focusing lens 19 which focuses the light beam at the liquid stream containing the particles or cells under investigation, and which will be described in more detail.

As each cell or particle passes through the focused light region where light beam 18 intersects the flowing liquid stream, light scattered by the cell or particle can be detected by an appropriate photodetector 21. Similarly, fluorescence, if emitted by particles energized by the illumination from the light source, can also be detected. Fluorescence emitted by autofluorescent particles or fluorescently labeled or stained particles in the liquid stream can be detected along the same axis as light beam 18 through lens 19, which, may, for example, be a condenser lens assembly. This lens assembly is preferably, but not necessarily, an epi-illuminating system which uses the same lens for imaging excitation light and for receiving fluorescence emission from the particles.

Fluorescence emitted by the flowing particles can be directed to a dichroic mirror 22 before being collected by fluorescence detector 24. More than one fluorescence detector may be employed in order to detect fluorescence emitted from the particles at different wavelengths. Photodetector 21 and fluorescence detector 24 are well-known photomultiplier tubes, or similar devices which convert light signals into electrical impulses, so that the light thereby detected may be associated with the fluorescently labeled cells and cells of a specific size flowing through the apparatus. The electrical signals from photodetector 21 and fluorescence detector 24 are typically fed to the electronics 28 of the apparatus for purposes of display 29, storage or further processing so that one or more characteristics of the cells or particles under analysis can be determined. Electronics 28 may be included in an analysis console 13, if desired.

Figure 3:
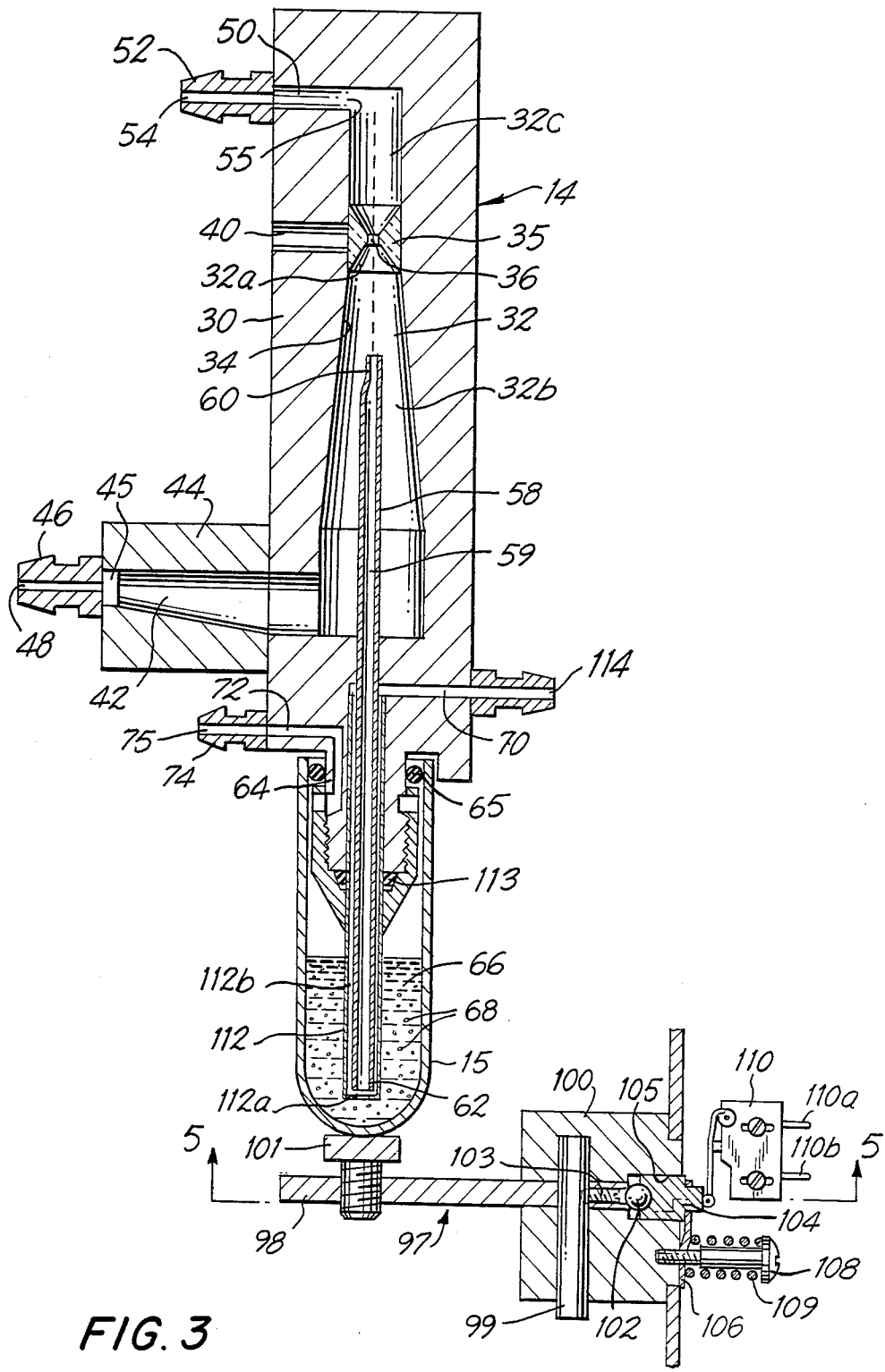
FIG. 3 is an enlarged cross-sectional view of the preferred flow housing and backflow isolator operator of the present invention taken along line 3—3 of FIG. 1.

Turning now to FIG. 3, the details of housing 14 of the present invention are more clearly illustrated. It can be seen that housing 14 includes a body member 30 which, in the embodiment being described, is preferably in the form of a block or rectangular prism. Although not shown in the drawings, the block form of housing 14 facilitates the mounting of the housing within the flow cytometer apparatus 10. Extending through housing 14 is a passageway 32 which is defined by three segments: an analysis portion 32a, a pre-analysis portion 32b, and a post-analysis portion 32c. As seen in FIG. 3, the pre-analysis, analysis and post-analysis portions of passageway 32 lie on the same axis through body member 30 and are arranged in that order relative to the direction of particle flow through the passageway 32.

It is preferred that analysis portion 32a and post-analysis portion 32c of the passageway be cylindrically shaped bores extending into body member 30. On the other hand, it is preferred that pre-analysis portion 32b of the passageway be tapered so that it includes tapered walls 34 defining a frustoconical passageway having its narrow end facing toward analysis portion 32a of the passageway.

Preferably positioned within analysis portion 32a of the passageway is a flowcell or flow chamber 35 which facilitates the analysis of cells or particles under investigation. Flowcell 35 includes an orifice 36 which is preferably sized to permit the passage of substantially one particle at a time therethrough. As a light beam intersects the region defined by orifice 36, particles pass through the light beam thereby establishing a basis for a light-related signal which can be detected.

So that light energy can be available to illuminate the region defined by orifice 36 in the flowcell, body member 30 of the housing includes a recess 38, as shown in FIG. 2, into which lens assembly 19 is positioned so that the lens assembly lies adjacent flowcell 35. This type of arrangement suggested by the illustration in FIG. 2 is consistent with a technique known as epi-illumination for providing light energy to interrogate the particles under analysis. Light is directed through lens assembly 19 at an angle substantially orthogonal or at a right angle to the aforementioned direction of particle flow through the flowcell. Lens assembly 19 can include one or more lenses in a condenser lens assembly for focusing incident light on the particles which pass through orifice 36 and may receive light such as fluorescence from the particles which have been illuminated by the incident light beam 18. Of course, the present invention contemplates that light from the particles may be detected in any direction with respect to the axis of the incident light beam.

The appropriate light detectors are positioned at the desired angle for collecting light scattered or emitted by the particles or for detecting light energy absorbed by the particles. To this end, as seen in FIG. 3, one or more windows 40 extend through body member 30 into flowcell 35 through which light passes for collection by the photodetector elements. On the other hand, it is not necessary to provide such a window if body member 30 is sufficiently light transmissive to allow light to pass therethrough in sufficient strength to be detected. It is, however, preferred that flowcell 35 be light transmissive and also that the flowcell be removable from body member 30 in the event that it needs cleaning, replacement or change.

Body member 30 also includes a first channel 42 which is in fluid communication with pre-analysis portion 32b of the passageway. Channel 42, in this embodiment, extends through a side block 44 of body member 30 so that this channel is substantially at right angles to the axis of passageway 32. Side block 44 includes a valve 45, or like device, which is operative to selectively open or close channel 42. Although not shown in FIG. 3, valve 45 can be operated manually, electrically, pneumatically or by any other convenient technique of operation. A fluid connector 46 is positioned on side block 44 so that its lumen 48 is in fluid communication with channel 42. It is the purpose of channel 42 to provide a passageway for the introduction of a liquid for sheathing particles which flow into analysis portion 32a of the passageway, and which more specifically flow through flowcell 35. The provision of a sheath liquid for a hydrodynamically focused fluid flow system is well-known and is described in the mentioned patents. The sheath liquid is generally pressured with air and typically flows through channel 42 at a pressure of between 0.5 and 10 psi and at a rate of 10 to 20 ml. per minute. The sheath liquid is usually a saline solution which is substantially particle free so that it does not interfere with the analysis.

Communicating with post-analysis portion 32c of the passageway is another channel 50 which also extends through body member 30 in the embodiment being described. Second channel 50 also preferably extends at substantially right angles to the axis of passageway 32. In fluid communication with channel 50 is a fluid connector 52 having a lumen 54 therethrough. It is the purpose of channel 50 to provide a passageway for the passage of particles and liquids out of housing 14 after passing through the analysis portion of the passageway. It can be seen that channel 50 has its interior end 55 preferably open to post-analysis portion 32c of the passageway.

Particles or cells to be analyzed are preferably transported through a hollow uptake tube 58 with a lumen 59 extending therethrough. Uptake tube 58 extends substantially long the axis of passageway 32 and has an inner end 60 positioned in pre-analysis portion 32b of the passageway. It is preferred that inner end 60 be positioned within tapered walls 34 of the pre-analysis portion so that the inner end 60 of the uptake tube lies adjacent flowcell 35 in the analysis portion of the passageway. Uptake tube 58 has its outer end 62 extending outwardly of body member 30. The body member of the housing preferably includes a circularly shaped extension 64 through which tube 58 extends before passing outwardly of the body member. A seal member 65, or other like element for providing a liquid-tight seal, is positioned around circularly shaped extension 64. It can be seen in FIG. 3 that test tube 15 is positioned so that it fits onto extension 64 with seal member 65 facilitating a liquid-tight seal between the test tube and extension 64 of the body member. Test tube 15 includes sampling liquid 66 and particles 68 to be analyzed. Outer end 62 of the tube extends into sampling liquid 66 in this embodiment.

In order to provide means for removing the backflow from end 62 of tube 58, a passageway 70 is provided around the exterior surface of uptake tube 58. Passageway 70 extends through extension 64 and communicates with the inside of test tube 15. A third channel 72 extends through body member 30 and is in fluid communication with the interior of test tube 15. A fluid connector 74 on the side of the body member includes a lumen 75 which is in fluid communication with channel 72. It is the purpose of connector 74 to be connected to a source of regulated pressurized air or other fluid to serve as a driving force of pressure into the test tube 15 so that sampling liquid 66 and particles 68 may pass through lumen 59 of uptake tube 58. Normally, the air is delivered through channel 72 at a slightly higher pressure than that applied to drive the sheath liquid through channel 42. In the preferred case, the regulated air pressure may be controlled at 5.0 psi or 4.0 psi for a selected high or low flow rate of 1.5 microliters per second, or 0.25 microliters per second, respectively.

Particles 68 pass out of the inner end of the tube into pre-analysis portion 32b of the passageway. Here, the particles and sampling liquid become ensheathed by the sheathing liquid so that the particles pass substantially one at a time through orifice 36 in flowcell 35, as seen in FIG. 3. The confluence between the sampling liquid (and particles) and the sheath liquid form a coaxial, bi-component stream. The sampling liquid containing the particles 68 to be analyzed forms the inner component of the flowing stream. When the stream enters the flowcell 35, there is substantial equilibration in the velocities of the sheath liquid and the sample liquid and the particles are hydrodynamically focused or centered in the middle of the stream away from the walls of the flowcell.

Once in the flowcell, the particles are interrogated by light which enters the flowcell through lens assembly 19 so that light-related information may be determined with respect to each particle. After the particles, sampling liquid and sheathing liquid pass through the analysi region of the passageway, flow continues through channel 50 for passage out of housing 14.

It is appreciated that the various air pressures and resulting flow rates could be manually adjusted by controls on the liquid sampling console. A typical sample flow rate is in the range of 0.25 to 1.5 microliters per second of sampling liquid through the sampling tube. Furthermore, the air pressure in channel 72 may be adjusted to control the count rate of particles through the flow chamber. Typically, the count rate would range between 100 and 1,000 particles per second flowing through the flow cell 35. The design of passageway 32 and the positioning of uptake tube 58 therein is intended to offer minimal flow resistance and turbulance to the bi-component stream of liquid as it flows toward flowcell 35.

In FIG. 4 there is a schematic illustration of the control 80 whereby the flow rate of particles 68 is regulated. The control 80 includes an air pump 82 connected to a pressure regulator 84 adjusted to provide a head pressure input of about 4.0 psi to the sheath liquid supply reservoir 86. The outlet from reservoir 86 is preferably connected to a filter 88 which removes any particulate matter from the sheath liqud as it is transported to the lumen 48 of housing 14.

Air pump 82, in FIG. 4, is also connected to the sample flow control 90 for providing pressurized air to be used to drive the liquid 66 and particles 68 through uptake tube 58 into pre-analysis portion 32b of housing 14. Sample flow control 90 regulates the air pressure applied to test tube 15 through lumen 75 so that the pressure is at 4 psi or 5 psi depending upon whether a low or a high flow rate of particles 68 is desired. A waste reservoir 92 as part of post-analysis portion 32c is connected to lumen 54 to collect the liquids and particles after they have passed through the passageway 32.

In FIGS. 1, 3, 4, and 5 the details of the backflow isolator and capture system are shown. The block diagram of FIG. 4 best illustrates the overall system 93. In particular, the test tube 15 has the driving air pressure supplied through lumen 75 to move particles through lumen 59 of the uptake tube 58. In lumen 75 immediately preceding its entry into test tube 15 is a valve 94 connected to direct air pressure from sample flow control 90 through lumen 75 into test tube 15 or to stop this flow and simultaneously connect test tube 15 to a safety vent filter 95 provided with an exit port 95a.

The valve 94 is preferably of the direct acting solenoid type such as the Asco®/Angar TM miniature solenoid valves from the Automatic Switch Company of Cedar Knolls, N.J. The valve is a three-way type operated by low voltage direct current such as about 12 volts and includes suitable fittings for connecting into lumen 75. In operation the valve is normally arranged to provide an air supply path from the sample flow control 90 to the test tube 15. By means of electrical switching, which will be explained, the valve 94 can be changed to permit flow from the test tube 15 through the lumen 75 and out through the safety vent filter 95. This change of the valve also closes the inlet from the sample flow control whereby purging of residual air pressure in test tube 15 can only take place by passing through the safety vent filter 95.

Since the samples in test tube 15 may include biohazardous material and a liquid carrier for that material, it is important to prevent aerosols and liquids from escaping into the atmosphere or leaving the system 93 in a way which could harm the researcher or other people in the vicinity. Consequently, filter element 96 is included within the safety vent filter 95 to prevent the passage of any biohazardous material. The preferred filter has a pore size of 0.2 microns and a filter surface area of about 19.6 square centimeters. The filter 96 is a hydrophobic polymeric membrane such as Teflon ® by DuPont, Wilmington, Del. which will not wet or pass water of normal system operating pressures and which has excellent temperature and solvent resistant characteristics. A preferred filter is the ACRO TM 50A hydrophobic filter sold by Gelman Sciences in Michigan.

Figure 5:
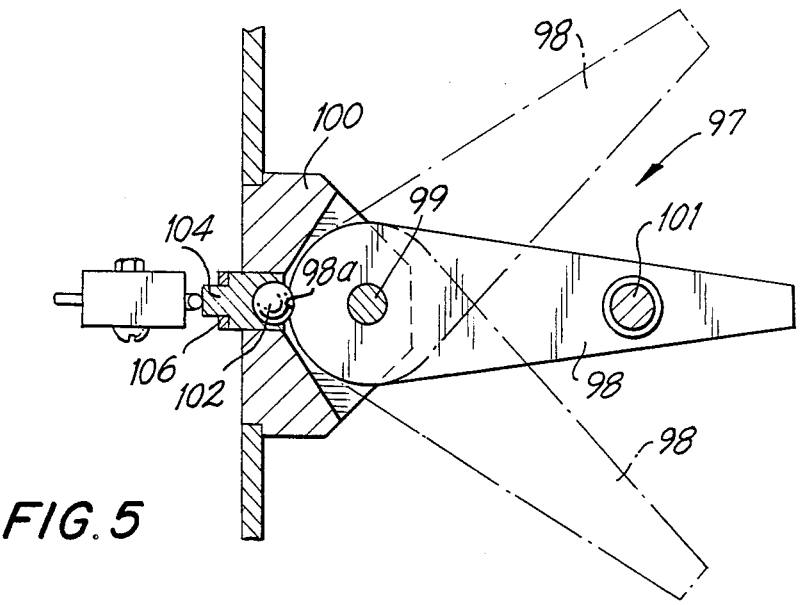
FIG. 5 is an enlarged partial cross-sectional view of the backflow isolator operator of the present invention taken along line 5—5 of FIG. 3.

In order to control the valve 94 there is a switch assembly 97 shown generally in FIGS. 1 and 4 and shown in detail in FIGS. 3 and 5. The operation of switch assembly 97 is best explained and understood with respect to the cross-sectional view shown in FIG. 3. A handle 98 is supported for pivotal movement about the axis of a pivot pin 99 to which handle 98 is secured by set screw 103. Pivot pin 99 is carried in support block 100. Handle 98 has an adjusting support screw 101 positioned to be located immediately below sample containing test tube 15. When the handle 98 is positioned as shown in FIG. 3, the test tube 15 is maintained in its position on the housing 14, in engagement with seal member 65. FIG. 5 shows alternate positions for the handle 98 achieved by pivoting the handle about the axis of the pivot pin 99. The alternate positions for the handle 98 are shown in broken lines and represent the handle condition whereat the test tube 15 can be removed from the apparatus. When the handle 98 is in the position as shown in FIG. 3 the test tube 15 is locked onto the apparatus 10 and cannot be removed without first pivoting handle 98.

For purposes of operating the backflow isolator there is a control portion of the handle 98 which is a camming surface 98a being a slight radial depression relative to pivot pin 99, see FIG. 5. A ball 102 cooperates with camming surface 98a. As is apparent in FIGS. 3 and 5, the rotation of the handle 98 will cause the ball 102 to move against a follower 104 carried in a follower bore 105 in block 100 such that the follower 104 moves as directed by the ball 102 into block 100.

In order to return the follower 104 there is lever arm 106 which bears against follower 104 at one end and against block 100 at the other end. A shouldered screw 108 threaded into block 100 carries a compression spring 109 which bears against the middle of lever 106 causing the follower 104 to be urged toward the ball 102. A portion of the follower 104 extend beyond the lever 106 for contact with a microswitch 110. The microswitch 110 is normally opened and movement of handle 98 in either direction from its center position shown in FIG. 5 will cause the follower 104 to close the microswitch 110 connecting any leads thereto at terminals 110a and 110b to be a complete circuit. The circuit is not shown in FIG. 3; it will be described in connection with the operation of system 93.

The backflow isolator system 93 acts to not only lock the test tube 15 to the housing but also to close the switch 110 while releasing the sample containing test tube 15. Closing the switch 110 provides power to operate the solenoid valve 94 changing the flow path from the sample flow control 90 to the test tube 15 to a path from the test tube 15 through the safety vent 95. Flow from the sample flow controller is shut off by valve 94. Also connected when switch 110 is closed is a pump motor assembly 111 shown in FIG. 4, the pump 111a being in fluid communication between reservoir 92 and a backflow capture tube 112. The activation of pump motor 111b occurs simultaneously with the operation of valve 94. The backflow capture tube 112 is preferably positioned concentrically about the uptake tube 58.

In the preferred embodiment the pump motor 111 is a compact peristaltic tubing pump such as the Barnant Company, Model 900-0626, 12 volt direct current three roller peristaltic action pump produced in Barrington, Ill. The surfaces of tube 112 should be wettable such as plasma etched polymers or oxidized metals since the system 93 seeks to clean remaining sample or residue. Wettable surfaces resist air bubbles which would hamper the drawing away of remaining material. A wettable tubing material for the pump 111a is Norprene a polymer which has excellent wettability and cooperates with the peristaltic pump to be a self priming arrangement that is easily cleaned. The self priming nature of a peristaltic pump acts to close the system preventing material remaining in the inlet portion of the pump tubing from backflow. Similarly, the positive nature of the way the pump clamps the tubing to force flow also acts as an anti-siphon device to prevent reverse or unwanted flow when the pump is off.

FIG. 3 shows the backflow capture tube 112 as positioned concentrically with respect to the uptake tube 58. This positioning establishes an annular passageway 112b between the outside of tube 58 and the inside of tube 112. There must be communication between the bottom of the test tube 15 and the extended and inwardly formed outer end 112a of the backflow capture tube 112 such that any remaining fluid in lumen 59 after removal of test tube 15 will be drawn away from the outer end 62 of the uptake tube 58 by the extended and inwardly formed outer end 112a of backflow capture tube 112. The tube 112 is held in the body member 30 by an O-ring 113 so that the tube 112 can be readily removed for cleaning and such that annular passage 112b connects for fluid communication with lumen 114.

In FIG. 4 lumen 114 is provided in pump inlet tube 115 whereby the fluid drawing force of pump 111 will cause a diminishment of pressure to occur within the extended and inwardly formed outer end 112a of the backflow capture tube 112 when the pump 111b is operating. An output pipe 116 forms the fluid communication between the pump 111a and reservoir 92 whereby captured material may be transferred to the reservoir for safe disposal. The reservoir 92 is a part of the post-analysis portion of the flow cytometer.

The closing of microswitch 110 by pivoting of handle 98 connects the circuit across terminals 110a and b and that closed circuit will produce an operating change in solenoid valve 94 to permit residual air pressure in tube 15 to pass through safety vent filter 95. The completed circuit will concurrently operate pump motor 111 to form a fluid drawing force at the extended outer end 112a of the backflow capture tube 112. Consequently, biohazardous materials which may remain in the lumen 59 or which may run off the exterior surfaces of capture tube 112 and which could drip or spatter, are drawn off by the pump 111a and disposed of in the reservoir 92. Similarly, any residual air pressure in test tube 15 will be safely vented through lumen 75 into safety vent filter 95 such that aerosols and harmful liquids do not escape.

Users of the apparatus 10 with system 93 are protected in that the simple pivotal movement of locking handle 98, to allow removal of the sample containing test tube 15, will cause the electrical circuitry to be completed operating both the valve 94 and the pump motor assembly 111 before removal of test tube 15 is possible. Thus the release of any hazardous material in the uptake tube 58 or in test tube 15 is prevented. The handle 98 functions as a safety lock to prevent the test tube 15 from being accidentally blown off of the extension 64 of housing 14 by the air pressure used to drive the sample up into the analysis portion of the apparatus. The test tube 15 is vented by the solenoid operated valve 94 when the handle 98 is pivotally removed from beneath the test tube.

The apparatus 10 with system 93 provides a safe means of isolating, capturing and containing biohazardous materials since the reservoir 92 may be a sealed container designed for easy removal and disposal.

What is claimed is:

1. A sample backflow isolator for a flow cytometer comprising:
    a body member having a passageway therethrough for the passage of particles which are to be analyzed, said passageway including an analysis portion, a pre-analysis portion and a post analysis;
    an uptake tube connected in fluid communication with said pre-analysis portion of said passageway and adapted for fluid communication with a test containing samples of particles for providing a flow path from the test tube into said flow cytometeranalysis portion;
    backflow capture means in fluid communication with said uptake tube and a pump for drawing fluid from said uptake tube after termination of flow from the test tube into said flow cytometer analysis portion;
    a filtered vent connected to the test tube by a valve to relieve air pressure supplied to the test tube for driving samples of particles through said pre-analysis portion to said analysis portion; and
    an operator disposed to lock the test tube to said body member and to change said valve means to connect said filtered vent to the test tube and to simultaneously activate said pump.

2. The backflow isolator of claim 1 wherein the analysis portion of said passageway includes a flowcell having an orifice size to permit the passage of substantially one particle at a time through said analysis portion, and wherein said backflow capture means is an outer tube concentrically positioned and arranged to encircle said uptake tube for drawing away residual samples, particles and backflow from said uptake tube.

3. The backflow isolator of claim 2 wherein said body member includes means for permitting light to be directed at said orifice at an angle substantially orthogonal to the direction of particle flow through said flowcell.

4. The backflow isolator of claim 3 wherein said means for permitting light includes a recess for positioning a lens adjacent said flowcell.

5. The backflow isolator of claim 2 wherein said filtered vent includes a filter capable of capturing aerosols or liquids released from said test tube when said valve means connects the test tube to said filtered vent.

6. The backflow isolator of claim 5 wherein said valve means includes an operator activated solenoid valve to close the air supply for pressurizing the test tube containing particles and to connect said filtered vent to safely release remaining air pressure in the test tube.

7. The backflow isolator of claim 6 wherein said pre-analysis portion includes a tapered segment which narrows toward said analysis portion, the inner end of said uptake tube being positioned within said tapered segment adjacent said analysis portion.

8. The backflow isolator of claim 7 wherein a sheathing liquid is introduced into said pre-analysis portion about said uptake tube inner end to provide a sheathed flow of particles along an axis of the passageway toward said analysis portion and away from said backflow capture means and the outer end of said uptake is within the extend end of said outer tube.

9. A backflow isolator for a particle flow through apparatus comprising:
    a body member having a passageway therethrough including an analysis region through which substantially one particle at a time may pass in a direction of sample flow when said apparatus is operating;
    a supply of particles connected in fluid communication with said passageway, for providing substantially one particle at a time to said analysis region;
    a sheathing liquid applied to said supply of particles in said passageway for hydrodynamic focusing the particles relative to said liquid;
    a backflow capture means associated with the passageway for drawing fluid from said passageway in a direction opposite of the direction of sample flow after the sample flow has been shut off; and
    a control means operatively associated with said backflow capture means and said supply of particles for selectively operating said backflow capture means to remove said particles remaining in or backflowing from said passageway and to permit said supply of particles to be removed from said passageway.

10. The backflow isolator of claim 9 wherein said backflow capture means includes a pump to draw fluid from said passageway and said control means includes an operator to activate said pump.

11. The backflow isolator of claim 10 wherein said operator is located to support the supply of particles in fluid communication with said passageway.

12. A backflow isolator for a flow cytometer comprising:
a body member having a passageway therethrough for the passage of particles which are to be analyzed, said passageway including an analysis portion, a pre-analysis portion and post-analysis portion, all of which lie on the same axis through said body member;
an uptake tube having an inner end postioned in said pre-analysis protion of said passageway adjacent the analysis portion and outer end extending outwardly of said body member for insertion into a pressurized sample supply containing liquid and particles, said uptake tube having a lumen extending therethrough for the passage of said particles toward the analysis portion of said passageway;
a flowcell included in said analysis portion and having an orifice sized to permit the passage of substantially one particle at a time through said analysis portion;
a backflow capture means associated with the passageway for drawing fluid from said passageway in a direction opposite of the direction of sample flow after the sample flow has been shut off; and
regulating means operatively associated with said backflow capture means for directing backflow captured from the uptake tube to the post-analysis portion.

13. A backflow isolator for a flow cytometer for determining one or more characteristics of particles or the like flowing in a liquid stream comprising:
means for moving particles in a liquid flow stream;
a body member having a passageway therethrough including an analysis region through which said moving particles pass substantially one at a time in the direction of flow;
a back flow capture means operative to draw off backflow from said passageway when said means for moving has been shut off;
means for providing a beam of light to illuminate said particles passing through said analysis region; and
means for detecting light with respect to each moving particle and for associating said detected light with one or more characteristics of each particle.

14. A method for isolating backflow through a particle flow through apparatus for transporting a sample of isolator operative when air pressure applied to the liquid is turned off including the following steps:
venting the air pressure applied to the liquid through a safety filter
concurrently with the venting step moving a supporting handle from a sample of particles, and
simultaneous with the venting step activating a pump connected to transport liquid and particles remaining in an analysis region to a disposal area of the particle flow through apparatus.

15. The method of claim 14 wherein the step of moving includes pivoting a support for the sample of particles carried in a liquid to release the sample for removal.

16. The method of claim 14 wherein the step of venting includes connecting the remaining applied air pressure by way of a valve to the safety filter.

17. The method of claim 16 wherein the step of connecting includes operating an electric solenoid valve.

18. The method of claim 16 wherein the step of activating the pump includes closing a switch by means of moving the support.

* * * * *